US009723973B2

(12) United States Patent
Dillon et al.

(10) Patent No.: US 9,723,973 B2
(45) Date of Patent: Aug. 8, 2017

(54) ENDOSCOPE MOUNTABLE VISUALIZATION DEVICE AND HANDLE

(71) Applicant: Cook Medical Technologies LLC, Bloomington, IN (US)

(72) Inventors: Travis Dillon, Winston-Salem, NC (US); Kenneth C. Kennedy, II, Clemmons, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 273 days.

(21) Appl. No.: 14/457,464

(22) Filed: Aug. 12, 2014

(65) Prior Publication Data
US 2015/0057537 A1 Feb. 26, 2015

Related U.S. Application Data

(60) Provisional application No. 61/867,853, filed on Aug. 20, 2013.

(51) Int. Cl.
*A61B 1/00* (2006.01)
*A61B 1/04* (2006.01)
(Continued)

(52) U.S. Cl.
CPC .......... *A61B 1/0014* (2013.01); *A61B 1/0052* (2013.01); *A61B 1/00066* (2013.01);
(Continued)

(58) Field of Classification Search
CPC ... A61B 1/0125; A61B 1/018; A61B 1/00154; A61B 1/0014; A61B 1/012; A61B 1/00137
(Continued)

(56) References Cited

U.S. PATENT DOCUMENTS 5,626,553 A 5/1997 Frassica et al.
5,863,286 A 1/1999 Yabe
(Continued)

FOREIGN PATENT DOCUMENTS

EP 0 664 991 A2 8/1995
JP 2002/078668 A 3/2002
(Continued)

OTHER PUBLICATIONS

International Search Report issued in corresponding application PCT/US2015/051984, dated Nov. 30, 2015, pp. 1-3.
(Continued)

*Primary Examiner* — Alexandra Newton
(74) *Attorney, Agent, or Firm* — Brinks Gilson & Lione (57) ABSTRACT

A dual medical endoscope system can be constructed including a first and a second medical endoscope, where the first endoscope comprises an accessory channel with a proximal mounting port providing access thereto, and where the second endoscope comprises a handle body that is securely and removably attached to the proximal mounting port. An endoscope, which may be the second endoscope, can include an elongate, manipulable shaft with a distal-end visualization element and a handle body comprising at least one control surface for manipulating a distal region of the shaft, where the handle body includes a passage through which a length of the shaft is passable, and where the handle body includes a connection structure configured for securely and removably mounting the handle to a channel of another endoscope in a manner axially aligning the passage with the channel to provide a path of communication for the shaft.

22 Claims, 9 Drawing Sheets

(51) Int. Cl.
*A61B 1/005* (2006.01)
*A61M 5/00* (2006.01)
*A61B 1/012* (2006.01)

(52) U.S. Cl.
CPC ........ *A61B 1/00128* (2013.01); *A61B 1/0125* (2013.01); *A61M 5/007* (2013.01)

(58) Field of Classification Search
USPC ....... 600/104, 112, 131, 153, 154, 156, 158, 600/159
See application file for complete search history.

(56) References Cited

U.S. PATENT DOCUMENTS

| | | | |
|---|---|---|---|
| 6,110,104 A | 8/2000 | Suzuki et al. | |
| 7,922,650 B2 | 4/2011 | McWeeney et al. | |
| 8,460,176 B2 | 6/2013 | McGrath | |
| 8,512,350 B2 * | 8/2013 | Ward | A61B 17/221 600/131 |
| 2003/0028096 A1 | 2/2003 | Niwa et al. | |
| 2004/0158127 A1 | 8/2004 | Okada | |
| 2004/0230268 A1 | 11/2004 | Huff et al. | |
| 2005/0033319 A1 | 2/2005 | Gambale | |
| 2005/0182292 A1 | 8/2005 | Suzuki | |
| 2005/0222494 A1 * | 10/2005 | Prescott | A61B 1/00096 600/113 |
| 2005/0267417 A1 | 12/2005 | Secrest | |
| 2006/0252993 A1 | 11/2006 | Freed et al. | |
| 2007/0270640 A1 | 11/2007 | Dimitriou et al. | |
| 2008/0097159 A1 | 4/2008 | Ishiguro | |
| 2009/0088600 A1 | 4/2009 | Meloul | |
| 2010/0228084 A1 | 9/2010 | Sato et al. | |
| 2010/0280311 A1 | 11/2010 | McGrath | |
| 2014/0114126 A1 | 4/2014 | Dresher | |
| 2015/0057537 A1 | 2/2015 | Dillon et al. | |

FOREIGN PATENT DOCUMENTS

| | | |
|---|---|---|
| JP | 2005296305 A | 4/2004 |
| JP | 2001 218733 A | 8/2011 |
| WO | WO 2009/029106 A1 | 3/2009 |
| WO | WP 2009/100106 A1 | 8/2009 |

OTHER PUBLICATIONS

International Search Report and Written Opnion mailed Aug. 2, 2010 for International Application No. PCT/US2010/032398.
Patent Examination Report No. 1 dated Dec. 21, 2012 for Australian Application No. 2010241834.

* cited by examiner

ENDOSCOPE MOUNTABLE VISUALIZATION DEVICE AND HANDLE

CROSS-REFERENCE TO RELATED APPLICATIONS

This application is a non-provisional application which claims priority to U.S. provisional application Ser. No. 61/867,853, filed Aug. 20, 2013, which is incorporated by reference herein in its entirety.

TECHNICAL FIELD

Embodiments disclosed herein generally relate to medical endoscopy devices. More particularly the embodiments relate to a steerable catheter including a distal visualization element.

BACKGROUND

Cholangioscopy is a minimally invasive endoscopic method used both for direct visual diagnostic evaluation of and for therapeutic intervention in the bile ducts. Peroral cholangioscopy overcomes some of the limitations of endoscopic retrograde cholangiopancreatography (ERCP) alone, although the procedures may be done together. Pancreatoscopy is the direct visual evaluation of the pancreatic ducts.

Figure 1A:
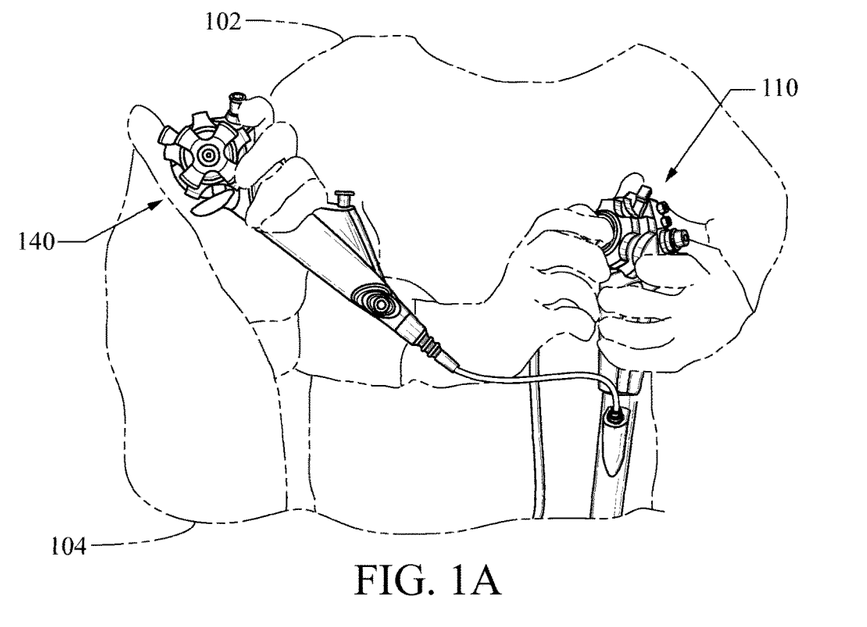
FIGS. 1A-1B show examples of known dual-endoscope configurations.

Although it has been in limited use since the 1950s, cholangioscopy has recently become more practically feasible, due in part to advances in endoscopic technique, scope design/materials, and functionality. However, cholangioscopes (and related smaller endoscopes that are dimensioned to be operated through a working channel of standard gastric endoscope, duodenoscope or the like, as well as within the bile ducts of a human patient, referred to as "miniscopes" or "baby scopes" where the larger scope is a "mother scope") have several limitations. For example, certain models require two endoscopists (see, e.g., FIG. 1A, where a first endoscopist 102 operates the "mother scope" 110, and a second endoscopist 104 operates the "baby scope" 140). This significantly increases the cost of procedures and complicates the logistics in smaller operating suites.

Figure 1B:
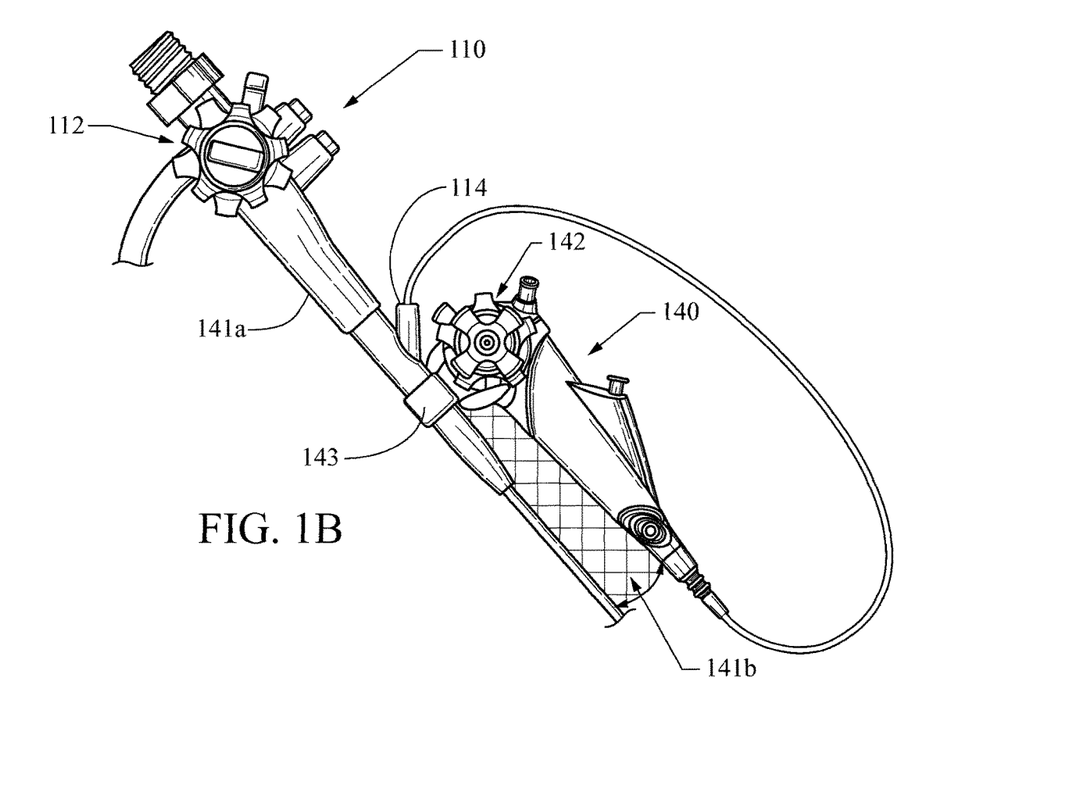

As shown in FIG. 1B, other miniscope models, although designed for use by a single endoscopist, may have control surfaces 142 for steering/manipulating and operating the miniscope 140 disposed offset at a significant distance from the control surfaces 112 of the larger endoscope 110 through which the miniscope 140 is situated. Those of skill in the art will appreciate that this can be uncomfortable for the user/endoscopist, as the position of the miniscope controls 142 is a significant distance away from the mechanical center of stability of the two-scope system, which center of stability is necessarily created by the endoscopist's left hand.

As a consequence, with this type of miniscope, forces impacting upon the system due to manipulation of the miniscope controls (and port features) create significant torsional moments about the center of stability at the endoscopist's left hand. This is due to the long moment arm through which these forces act. These torsional moments must be resisted by the left hand of the endoscopist, and can create difficulty with control as well as operator fatigue. In addition, the strap-mounting structure 143 used for mounting such a miniscope 140 below the mother scope's accessory channel 114 leaves a prominent gap 141a between the two endoscopes' control surfaces, as well a prominent cross-hatched gap region 141b between the two endoscopes bodies, which (due in part to the relative body lengths compared to the length of attachment region) can create an unstable coupling, such that—under the typical forces of manipulation—this type of miniscope may rock, shift, slip downwards, or pivot about the primary axis of the larger "mother scope" (e.g., duodenoscope). These movements can create additional difficulty, stress, and fatigue for the endoscopist, which can have a negative impact.

Cholangioscopy is known to be an effective diagnostic and therapeutic tool, and there is a need for providing a miniscope that addresses needs in the existing art while providing technology that is diagnostically effective, therapeutically effective, and cost-effective. It may be desirable to provide a miniscope, configured for use in cholangioscopy or other dual-endoscope procedures that provides a secure, rigid mounting of two scopes together, with control surfaces provided and located to promote ease of efficient operation.

BRIEF SUMMARY

In one aspect, embodiments disclosed herein may include a dual medical endoscope system including a smaller scope attached to and extending partially through a larger scope, with methods for assembling, disassembling, and using the same for medical observational, diagnostic, and/or therapeutic methods.

In one aspect, embodiments of a medical endoscope disclosed herein may include an elongate, manipulable shaft including a distal-end visualization element; and a handle body comprising at least one control surface for manipulating a distal region of the shaft; where the handle body includes a passage through which a length of the shaft is passable; and where the handle body includes a connection structure configured for securely and removably mounting the handle to a channel of a second endoscope in a manner axially aligning the passage with the channel to provide a path of communication for the shaft.

In certain aspects embodiments may include a dual medical endoscope system, with a first medical endoscope and a second medical endoscope, where the first medical endoscope includes an accessory channel with a proximal mounting port providing access thereto, and where the second medical endoscope includes a handle body that is securely, and removably attached to the proximal mounting port.

In other aspects, embodiments may include a method for performing a dual-endoscope procedure, where the method includes steps of: providing a first, larger, endoscope and a second, smaller, endoscope; where the larger endoscope includes an accessory channel with proximal engagement structure providing direct access to the channel, where a distal shaft of the second endoscope is sized for passage through the channel, and where the second endoscope includes a connection structure configured for securely and removably mounting a handle of the second endoscope directly to the proximal engagement structure of the first endoscope's accessory channel; and directing a distal shaft of the first endoscope to a target region; and directing the distal shaft of the second endoscope through the channel of the first endoscope.

Certain embodiments, in another aspect, may relate to a medical endoscope with an elongate, manipulable shaft including a distal-end visualization element; and a handle body comprising at least one control surface for manipulating a distal region of the shaft; where the handle body includes a structure through which a length of the shaft is passable; and where the handle body includes a connection structure configured for securely and removably mounting the handle to a channel of a second endoscope in a manner axially aligning the passage with the channel to provide a path of communication for the shaft.

BRIEF DESCRIPTION OF THE DRAWINGS

FIGS. 6-6C show a first connection structure embodiment;

DETAILED DESCRIPTION

Various embodiments are described below with reference to the drawings in which like elements generally are referred to by like numerals. The relationship and functioning of the various elements of the embodiments may better be understood by reference to the following detailed description. However, embodiments are not limited to those illustrated in the drawings. It should be understood that the drawings are not necessarily to scale, and in certain instances details may have been omitted that are not necessary for an understanding of embodiments disclosed herein, such as—for example—conventional fabrication and assembly.

An in-vivo visualization device configured for viewing and/or performing diagnostic and therapeutic procedures within the human body, such as in the biliary tree, may include a steerable catheter shaft with a distal visualization modality (e.g., a complementary metal oxide silicon (CMOS) sensor). The device may be configured as an endoscope in the manner of a so-called miniscope or "baby scope" operable through the accessory channel of a larger "mother scope" (e.g., a duodenoscope). In particular, the device may be configured to be securely, rigidly, and removably attached directly to the proximal mounting port of an accessory channel of the mother scope with the steerable shaft of the device disposed through that channel. By "rigidly," the present disclosure refers to a substantially solid and inflexible connection where the "baby scope" remains in a substantially fixed orientation relative to the "mother scope" without flexing or otherwise moving relative thereto unless the connection is released, (e.g., specifically in contrast with known devices that allow flexure between the handle bodies of two attached scopes). As such, in one aspect, embodiments of the present disclosure may include a dual endoscope system.

In one aspect, presently disclosed embodiments address the need in the art for a dual endoscope system to perform cholangioscopy and/or other procedures for diagnostic and therapeutic purposes. In particular, the need is addressed for such a system that locates the control surfaces of a primary endoscope and the control surfaces of a secondary endoscope in close proximity, with the secondary endoscope securely, rigidly, and removably attached directly to the proximal mounting port of an accessory channel of the primary endoscope. The attachment provides for operation of a manipulable shaft of the secondary endoscope through the accessory channel of the primary endoscope.

The invention is defined by the claims, may be embodied in many different forms, and should not be construed as limited to the embodiments set forth herein; rather, these embodiments are provided so that this disclosure will be thorough and complete, and will fully convey enabling disclosure to those skilled in the art. As used in this specification and the claims, the singular forms "a," "an," and "the" include plural referents unless the context clearly dictates otherwise.

The terms "proximal" and "distal" are used herein in the common usage sense where they refer respectively to a handle/doctor-end of a device or related object and a tool/patient-end of a device or related object. The term "Luer-type" is used to refer to (and includes) Luer taper or similar fluid-tight fitting engagement interfaces that are engageable to form a tight connection based upon the angles of interfacing surfaces, well-known in the art, and includes engagement structures known as "Luer lock" connections. Luer-type connections, threaded connections, bayonet-style connections, frictional slide-clamps, snap-fit, set-screws, and other connection interfaces useful in attaching two generally tubular structures are so well known in the art that the present disclosure does not belabor all the variants and combinations thereof, although each of them (alone or in combination with other connection means—whether listed or not) may be used within the presently disclosed embodiments. Cholangioscopy is a specific intraductal endoscopic technique. The structures and methods disclosed herein may be useful in a variety of diagnostic and therapeutic endoscopy procedures, and may particularly be useful during cholangioscopy, whether conducted alone or in conjunction with ERCP (endoscopic retrograde cholangiopancreatography). The intracorporeal aspects of dual-scope procedures (e.g., endoscopic retrograde cholangiopancreatography, endoscopic retrograde cholangiography, cholangioscopy, and others) are very well characterized in the medical endoscopy art, such that reference to such procedures herein will be fully comprehended by those of skill in the art given the focus of the present disclosure upon extracorporeal connection structures of an endoscope (described and claimed herein) to a second endoscope (which may be a standard endoscope not claimed herein, or part of a system incorporated in the presently disclosed and claimed subject matter).

Figure 2A:
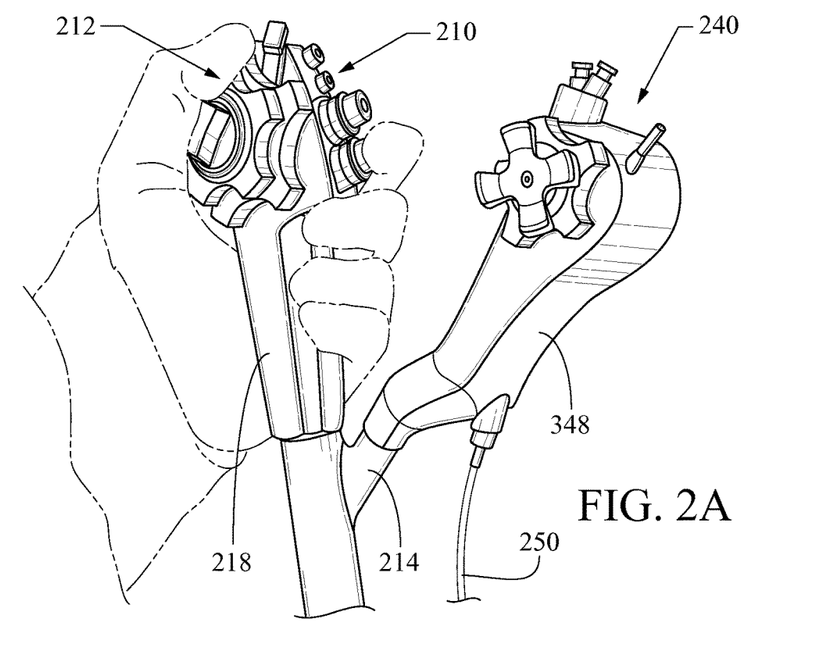
FIGS. 2A-2B, show two perspective views of a larger endoscope and a smaller endoscope (miniscope)
Figure 2B:
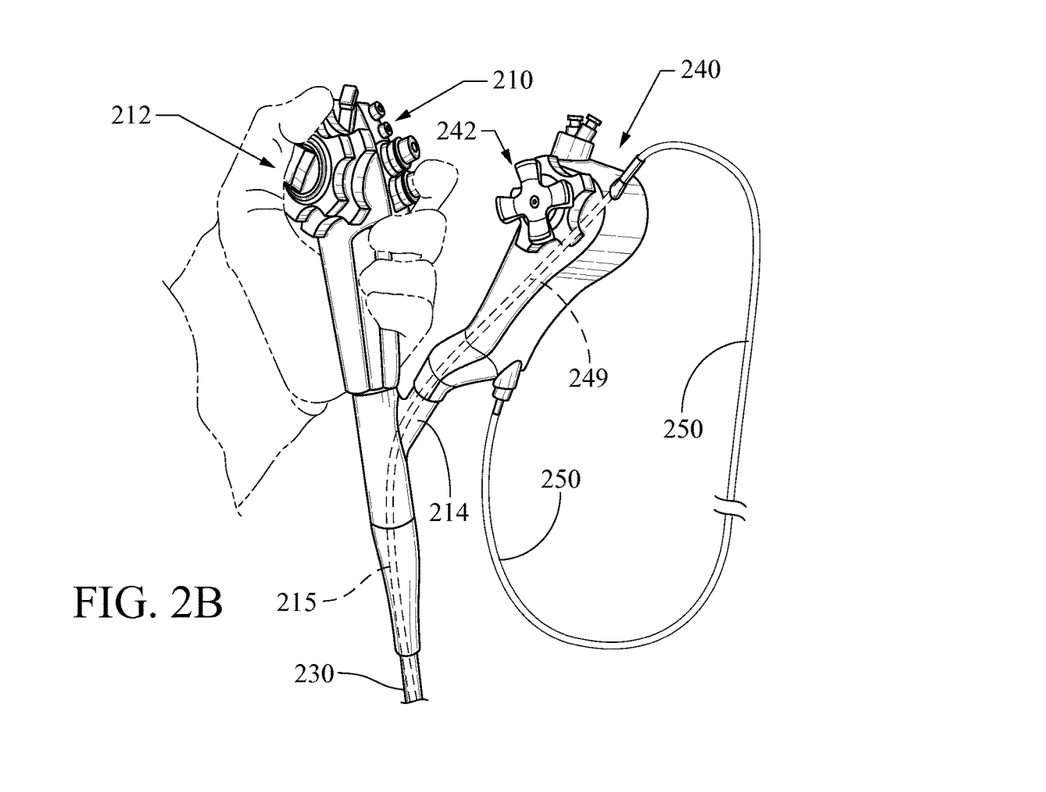
Figure 4:
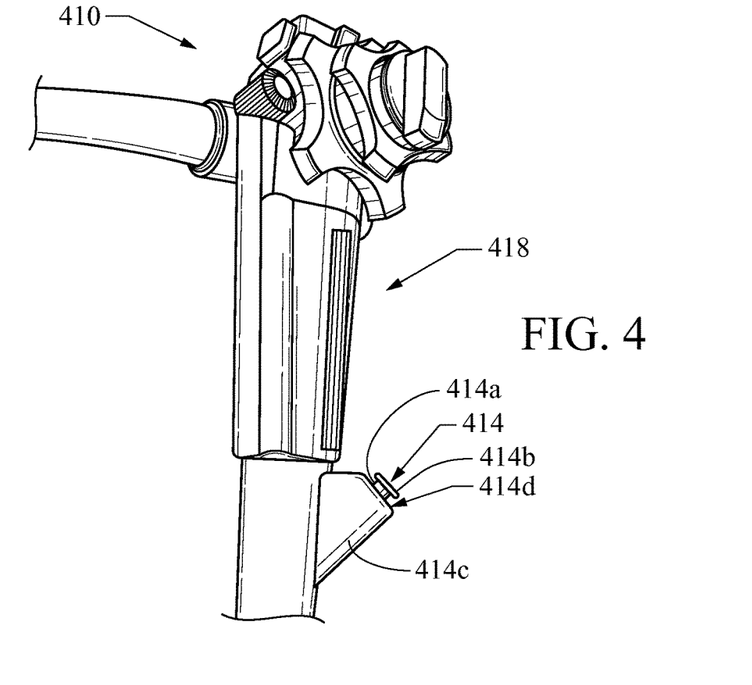
FIGS. 4-5 show two examples of endoscope accessory port configurations.
Figure 5:
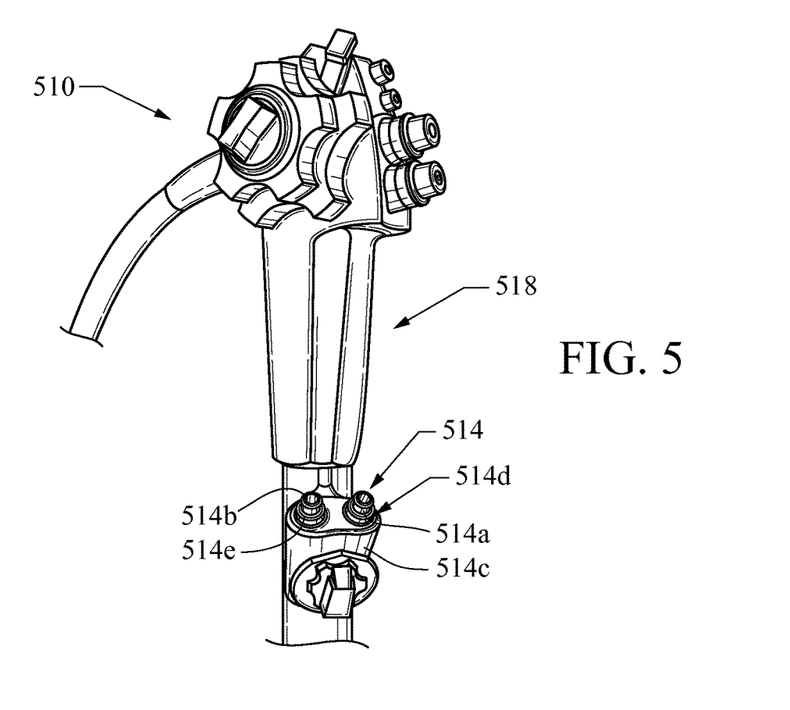

One embodiment of a medical endoscope system is described with reference to FIGS. 2A-2B, which show, respectively, two perspective views of a larger first endoscope 210 and a smaller second endoscope (miniscope) 240. The handle body 248 of the miniscope 240 is securely and removably attached directly to the accessory port portion 214 of the first endoscope 210. FIGS. 4-5 show exemplary accessory port structures 414 and 514 of different larger endoscopes. Those of skill in the art will appreciate, with reference to the present disclosure (including, for example, FIGS. 6-9) and the state of the art, that the miniscope 240 may be directly, securely, rigidly, and removably and adjustably attached to different accessory port configurations as those configurations may vary across different types (e.g., by medical application and/or by manufacturer) of larger endoscopes. The term "adjustably" in this context refers to the adjustability of the miniscope's connection with respect to axial rotation of the miniscope around the long axis of its handle and/or the long axis of its connection with a larger scope (which, in many embodiments, may be defined by the miniscopes' shaft body).

The first endoscope 210 includes a handle body 218 with proximal/upper-end control surfaces 212 for operation (e.g., manipulation of the shaft and control of visualization elements). In the illustrated embodiment, the miniscope 240 also includes control surfaces 242 for operation (e.g., manipulation of the shaft and control of visualization elements). In certain embodiments, at least one control surface of the smaller endoscope 240 is configured substantially similarly to at least one control surface of the first endoscope 210. It may be preferable that all control surfaces are configured substantially similarly or even exactly the same so that an endoscopist can readily operate both scopes with the same relative motions generating the same relative response of the distal shaft and other elements. The proximity and similar orientation of both scopes' control surfaces 212, 242 will promote efficiency and ease of operation.

The miniscope 240 includes an elongate shaft 250 that preferably is manipulable in at least two, and preferably at least three, dimensions and that includes at or near its distal end a visualization element such as, for example, a CMOS sensor. Specific elements of the control surfaces, shaft manipulation/steering means, shaft lumens, and other features may be configured similarly to other endoscopy devices, or may have unique, novel configurations not described herein. The shaft 250 extends from a lower/distal end of the miniscope handle body 248 and loops back around to pass via a miniscope handle passage 249 through the accessory port (not shown) into the accessory channel 215 of the larger scope 210. The miniscope shaft 250 is dimensioned so that it will extend through the accessory channel 215 and out of a distal end of the first endoscope shaft 230, preferably be freely slidable therethrough to allow longitudinal manipulation by a user in the manner desired (e.g., for cholangioscopy).

Figure 3:
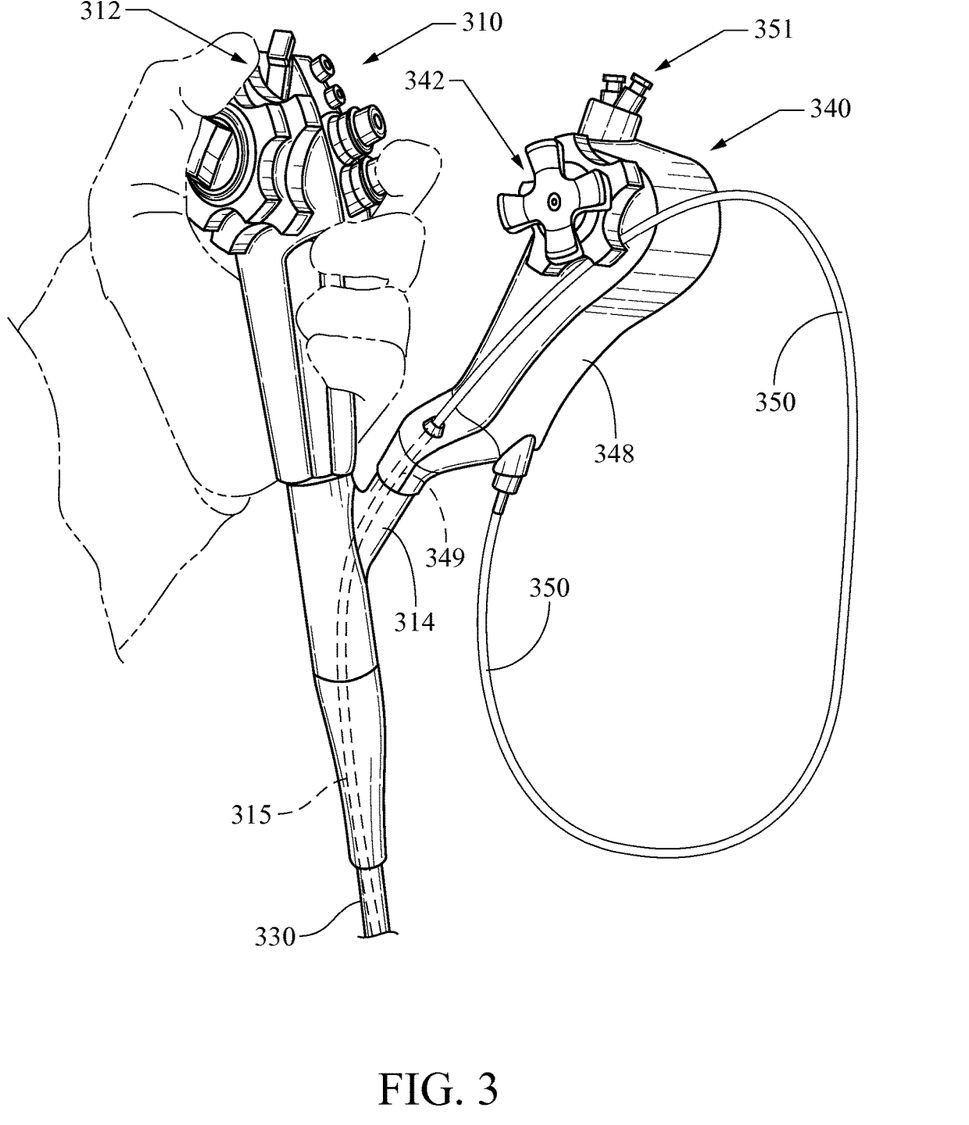
FIGS. 3-3A each shows a dual-endoscope assembly where each smaller endoscope embodiment includes an offset handle portion relative to a shaft passage.

In another embodiment of a medical endoscope system, shown in FIG. 3, a miniscope 340 may be provided with a handle body 348 providing a handle passage 349 that extends through only a minor length (less than about one-half the length) of the handle body 348. In this embodiment, a portion of the handle body 348 is axially offset relative to the handle passage 349 and the connection structure, such that the passage extends through less than a majority length of the handle body 348. In another embodiment, the passage may be configured as a structure outside the handle body (e.g., a clip or other guide structure), where the handle body is secured to the larger scope 310 by a structure not engaging directly into or around an aperture of the accessory port portion 314 (see, e.g., wrap 859 in FIG. 8A, which can be adapted to provide secure attachment without requiring direct engagement with a tubular working channel aperture 814a so that an offset-body miniscope handle can be used; specifically, such an embodiment may include a wrap 859 and a handle body 348, with the handle body 348 engaged only to and by the wrap 859 but lacking engagement around the working port aperture).

In the embodiment of FIG. 3, a larger first endoscope 310 and a smaller second endoscope (miniscope) 340 are shown. The handle body 348 of the miniscope 340 is securely, removably, and adjustably attached directly to the accessory port portion 314 of the first endoscope 310. The first endoscope 310 includes control surfaces 312 for operation (e.g., manipulation of the shaft and control of visualization elements). In the illustrated embodiment, the miniscope 340 also includes control surfaces 342 for operation that preferably are configured substantially similarly to at least one control surface of the first endoscope 310.

The miniscope 340 includes an elongate catheter shaft 350 that preferably is manipulable in at least two or (more preferably) three dimensions and that—in this and other embodiments—may include one or more other channels/lumens (e.g., for passage therethrough of guidewire(s), therapeutic and/or diagnostic tools, fluids (e.g., radiopaque contrast, flushing fluid), and/or other materials), accessible through one or more ports 351 on the proximal region of the handle body 348. The miniscope 340 may also include at or near its distal end a visualization element (not shown) such as, for example, a CMOS sensor. Specific elements of the control surfaces, shaft manipulation/steering means, shaft lumens, and other features may be configured similarly to other endoscopy devices, or may have unique, novel configurations not described herein. The shaft 350 extends from a lower/distal end of the miniscope handle body 348 and loops back around to pass via the offset miniscope handle passage 349 through the accessory port 314 into the accessory channel 315 of the larger scope 310. The miniscope shaft 350 is dimensioned so that it will extend through the accessory channel 315 and out of a distal end of the first endoscope shaft 330, and preferably will be freely slidable therethrough to allow longitudinal manipulation by a user in the manner desired. In this embodiment, the miniscope shaft 350 will have less frictional contact with the handle body than may be present in other embodiments. This will also allow a user readily to longitudinally manipulate the miniscope shaft 350 from a familiar position/orientation of gripping and manipulating the miniscope shaft (e.g., relative to prior devices shown in FIGS. 1A-1B).

Figure 3A:
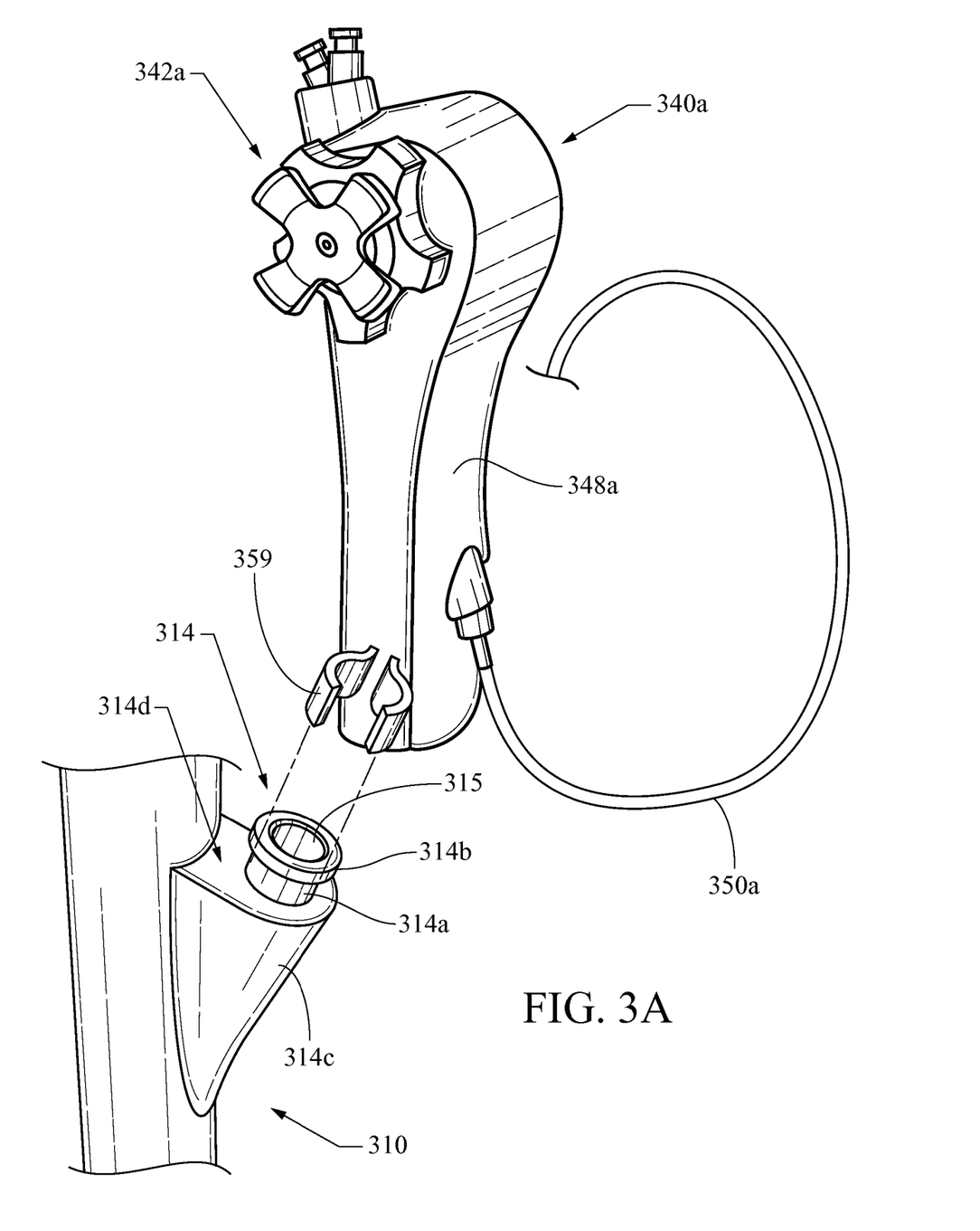

In the embodiment of FIG. 3A, the larger first endoscope 310 is shown with a smaller second endoscope (miniscope) 340a. The handle body 348a of the miniscope 340a is securely, removably, and adjustably attachable directly to the accessory port portion 314 of the first endoscope 310. In the illustrated embodiment, the miniscope 340a also includes control surfaces 342a for operation that preferably are configured substantially similarly to at least one control surface of the first endoscope 310.

The miniscope 340a includes an elongate catheter shaft 350a that preferably is manipulable in at least two or (more preferably) three dimensions. The shaft 350a is shown truncated, but—in this and other embodiments—may include one or more other channels/lumens (e.g., for passage therethrough of guidewire(s), therapeutic and/or diagnostic tools, fluids (e.g., radiopaque contrast, flushing fluid), and/or other materials), accessible through one or more ports on the proximal region of the handle body 348a. The miniscope 340a may also include at or near its distal end a visualization element (not shown) such as, for example, a CMOS sensor. Specific elements of the control surfaces, shaft manipulation/steering means, shaft lumens, and other features may be configured similarly to other endoscopy devices, or may have unique, novel configurations not described herein. The shaft 350a extends from a lower/distal end of the miniscope handle body 348a and loops back around to pass alongside the offset miniscope handle body 348a through the accessory port 314 into the accessory channel 315 of the larger scope 310. The term "offset" refers to the alignment of the long axis of the miniscope handle body 348 relative to the long axis of the larger scope's accessory port 314 when the clip is engaged thereabout.

The miniscope shaft 350a is dimensioned so that it will extend through the accessory channel 315 and out of a distal end of the first endoscope shaft, and preferably will be freely slidable therethrough to allow longitudinal manipulation by a user in the manner desired. In this embodiment, the miniscope shaft 350a will have less frictional contact with the handle body than may be present in other embodiments. This will also allow a user readily to longitudinally manipulate the miniscope shaft 350a from a familiar position/orientation of gripping and manipulating the miniscope shaft (e.g., relative to prior devices shown in FIGS. 1A-1B).

The larger endoscope's accessory port 314 extends from a side of its lower/distal handle portion. It includes a cylindrically tubular metal body 314a with a protruding annular lip 314b. A base 314c of the port includes a flat surface 314d generally perpendicular to the central long axis of the tubular port body 314a. In this embodiment, a connection clip assembly 359 of the miniscope handle 348a is configured to engage around the tubular port body 314a between the annular lip 314b and the flat surface 314d to hold the miniscope handle rigidly, adjustably, securely, and removably to the larger scope handle in a manner that aligns the passage of the miniscope with the port and the accessory channel 315 to permit transit therethrough of the miniscope shaft 350a.

Two examples of accessory port structures of larger ("mother") endoscope embodiments are shown in FIGS. 4-5. Those of skill in the art will appreciate that different types of endoscopes (e.g., duodenoscopes, bronchoscopes, colonoscopes, etc.) may have different accessory channel port configurations, which may vary by the scopes' makers and/or uses. Different embodiments of the present disclosure may include miniscopes, handles, and connection structures configured for connection with any of those accessory port designs, and practiced within the scope of the present disclosure and claims.

FIG. 4 shows one example of a handle 418 of a duodenoscope 410. The accessory port 414 extends from a side of the lower/distal handle portion. It includes a cylindrically tubular metal body 414a with a protruding annular lip 414b. A base 414c of the port includes a flat surface 414d generally perpendicular to the central long axis of the tubular port body 414a. For this type of port structure, a connection portion of a miniscope of the present disclosure may include structure that engages the annular lip 414b and the flat surface 414d to hold the miniscope handle rigidly, securely, and removably to the larger scope handle 418 in a manner that aligns the passage of the miniscope with the port and the accessory channel to permit transit therethrough of the miniscope shaft. In one aspect of each of the embodiments disclosed herein, a miniscope handle portion may engage into the inner diameter of (and/or around the outside diameter of) the tubular port body 414a (in the manner shown by way of example of handle body extension 648x into the inner diameter of the larger scope's working channel, shown in FIG. 6C, or in another manner).

FIG. 5 shows an example of a handle 518 of a colonoscope 510. The accessory ports 514 extend from a side of the lower/distal handle portion. They each include a cylindrically tubular metal body 514a with a protruding annular lip 514b and a protruding annular ring 514e near the where the exposed metal tubular body meets the base 514c of the port at a flat surface 514d generally perpendicular to the central long axis of the tubular port body 514a. For this type of port structure, a connection portion of a miniscope of the present disclosure may include structure that engages the flat surface 514d and one or both of the annular lip 514b and the annular ring 514e to hold the miniscope handle rigidly, securely, and removably to the larger scope handle 518 in a manner that aligns the passage of the miniscope with the port and an accessory channel to permit transit therethrough of the miniscope shaft. In some embodiments, the annular lip may be configured as a Luer type connector element or a threaded connector element for securing items to the port in a manner that preferably will—like the other connections described herein—maintain a seal (e.g., to maintain patient insufflation, prevent escape/leakage of patient body fluids, etc.).

FIGS. 6-9 show embodiments of connection structures of a miniscope configured for securely and removably mounting the miniscope handle to an accessory port channel of a second endoscope in a manner axially aligning the miniscope shaft passage with the second endoscope's accessory channel to provide a path of communication for the miniscope shaft therethrough. Several embodiments include levered clip engagement structures, where the levering structure of a miniscope that engages/disengages a clip or other element from an accessory channel structure of a larger scope may be a pivoting arm, a rotary collar element, or any combination thereof. It should be appreciated that various features of the following structures may be interchangeable between embodiments, within the scope of the present disclosure.

Figures 6, 6A, 6B, 6C:
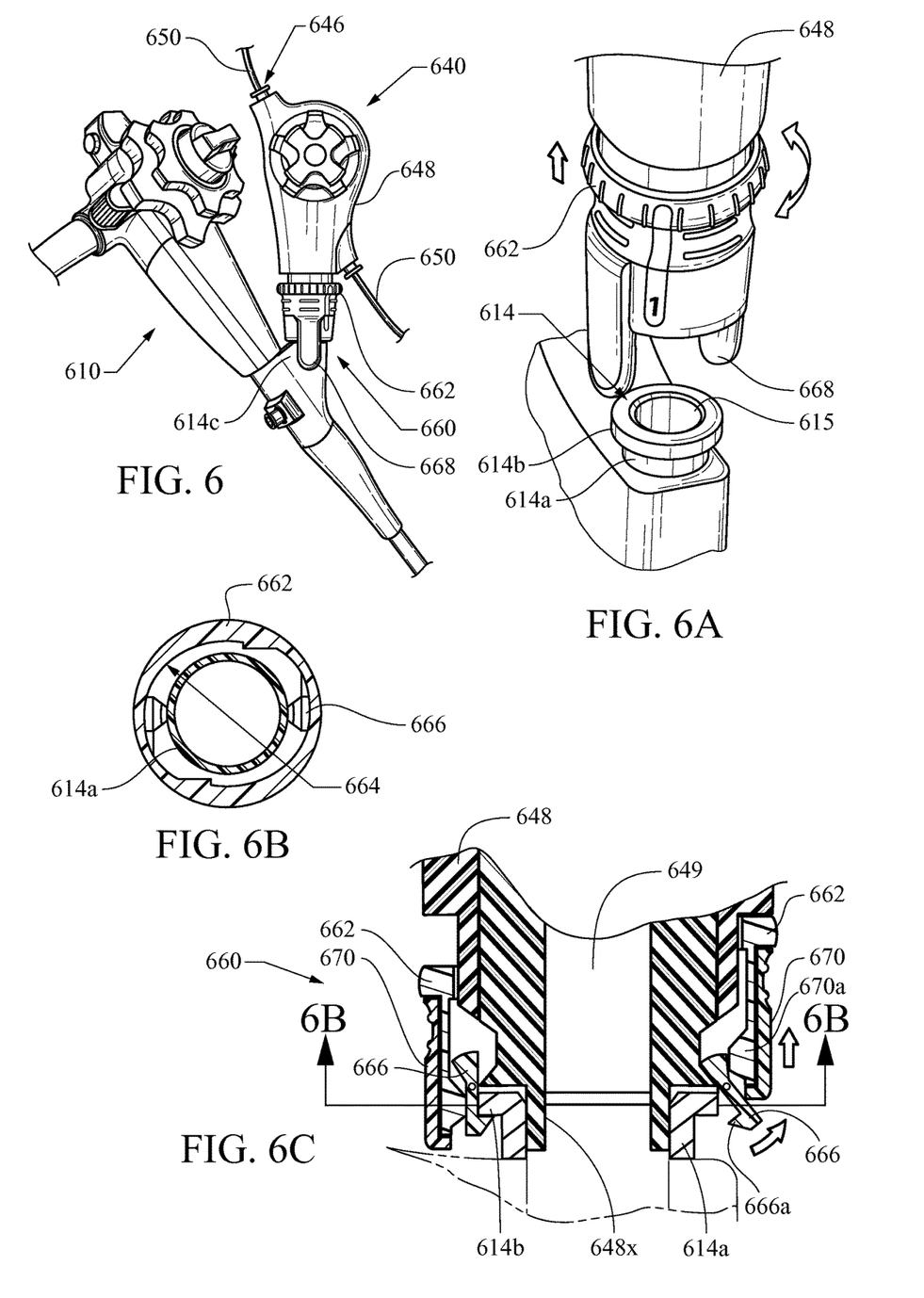

FIG. 6 shows a first connection structure embodiment 660 as part of a miniscope 640 that is securely and rigidly, but removably and adjustably, attached to a larger endoscope 610. FIGS. 6A-6C show the structure and function of the first connection structure 660, which includes a rotary collar 662 that can be rotated to adjust the internal dimensions of the connection structure 660 relative to the miniscope handle body 648 to accommodate different models of a larger endoscope 610. A ramped/cammed inward-facing surface 664 of the rotary collar is shown from a transverse section view in FIG. 6B (taken along line 6B of FIG. 6C). The inward-facing collar surface 664 rotates to change the inner diameter accommodated by two or more pivoting clip arms 666 (there may be three, four, or more clip arms to provide a securely rigid connection, which pivot and/or are levered for engagement as described herein). The collar 662 is securely attached to a clip arm sleeve 670, and—together—the two elements are longitudinally slidable (or otherwise longitudinally movable, whether in linear or rotary fashion). The device may include visual or other indicia showing a rotary position corresponding to a specific model/size of "mother scope" 610.

The clip arms 666 are, in turn, configured securely to engage the annular lip 614b of the tubular metal body 614a of the accessory port 614. As shown in this embodiment (and applicable to variants of other embodiments), connection means may include an extension 648x of the miniscope handle body 648, which may be configured to fittingly engage into the inner diameter of the tubular body 614a to provide further securing support to the engagement of the miniscope 640 with the larger scope 610. A pair of fixed location legs 668 of the connection structure 660 fit firmly and securely to the base 614c of the accessory port 614. The clip arms 666 may be engaged or disengaged as shown, respectively, in the left and right sides of FIG. 6C. It will be appreciated that the left side of FIG. 6C shows an engaged configuration where the clip arm sleeve 670 is slid downward (which position will be mirrored relative to all other clips of a single embodiment in that engaged configuration), while the right side of FIG. 6C shows a disengaged configuration where the clip arm sleeve 670 is slid upward (which position will be mirrored relative to all other clips of a single embodiment in that disengaged configuration).

In the upward/retracted/disengaged position, the clip sleeve 670, and particularly the inward facing portion of the clip sleeve/collar assembly, pivotingly rocks the clip arms 666 upward such that a protruding lower lip 666a thereof is disengaged from below the annular lip 614*b* of the port 614. As will be appreciated by those of skill in the art with reference to FIGS. 6B and 6C, the mechanism illustrated and described can also be As shown in FIG. 6C, when the connection structure 660 is engaged to the port 614, the miniscope handle passage 649 is aligned with and secured to the accessory channel of the larger scope 610. This will allow operation of the miniscope catheter shaft body 650 through the accessory channel. Specifically, as indicated in FIGS. 6A and 6C, the clip arm locking sleeve 670 is longitudinally slidable relative to the miniscope passage 646 and includes cammed surface(s) 670*a* that pivotingly engage the clip arms 666, contacting them so that those clip arms will engage under or disengage from the annular lip 614*b*. It should be appreciated that, for an accessory port like that shown in FIG. 5, the clip arms may be shaped to engage one or both of the annular lip 514*b* and the annular ring 514*e*.

Figure 7:
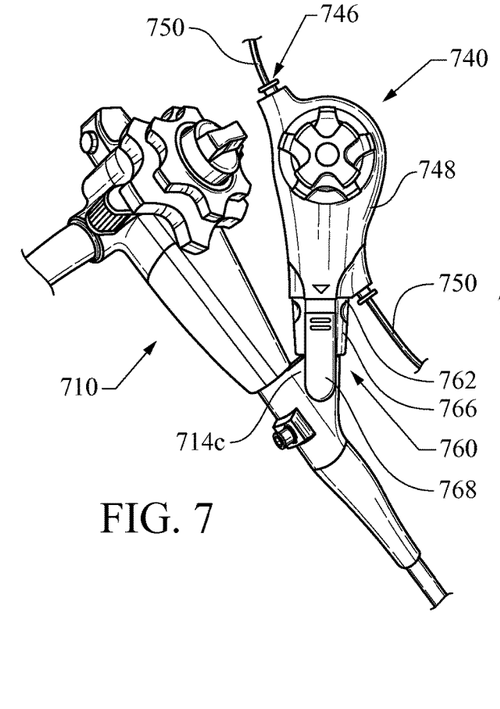
FIGS. 7-7C show a second connection structure embodiment.
Figure 7A:
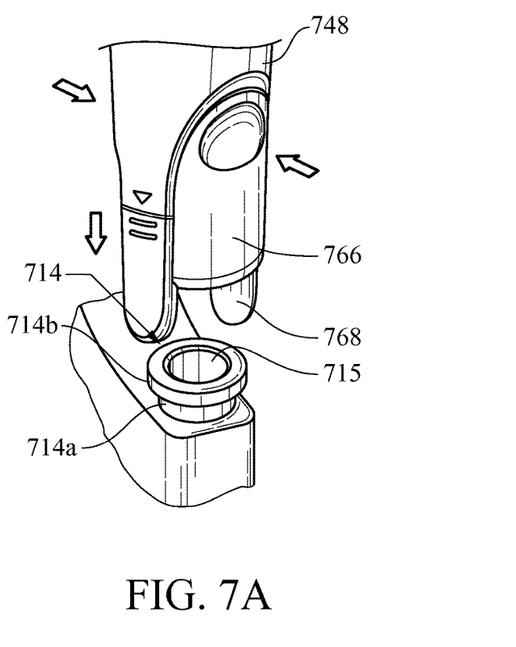
Figure 7B:
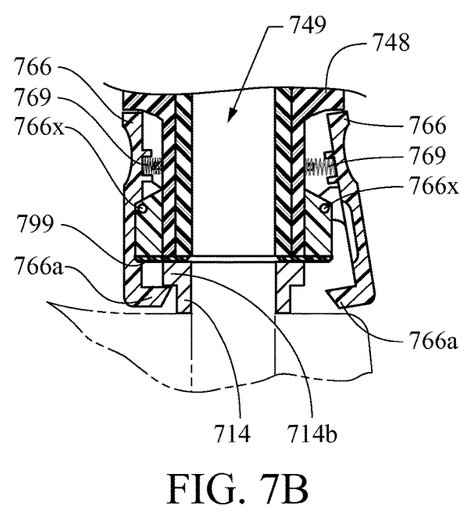
Figure 7C:
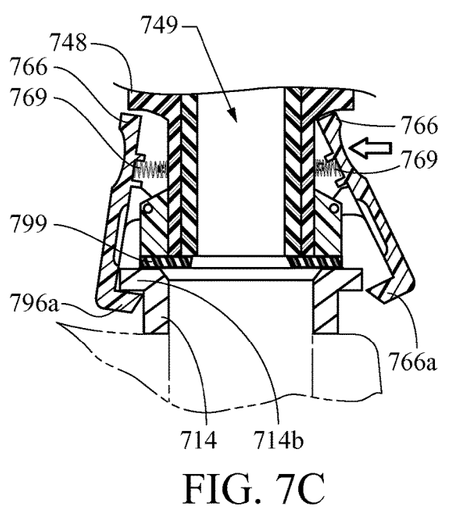

FIG. 7 shows a second connection structure embodiment 760 as part of a miniscope 740 that is securely and rigidly but, removably and adjustably, attached to a larger endoscope 710. FIGS. 7A-7C show the structure and function of the second embodiment of a connection structure 760, which includes a pair of pivoting clip arms 766 extending down from the miniscope handle body 748. The clip arms 766 are biased to pivot across a pivot axis 766*x* in a manner that securely engages the annular lip 714*b* of the tubular metal body 714*a* of the accessory port 714. As such, they may be viewed as levered with a fulcrum. The clip arms 766 may be engaged or disengaged as shown, respectively, in the left and right sides of FIGS. 7B and 7C, which show—respectively—a smaller-diameter and a larger-diameter accessory port 714, with the manner in which the embodiment firmly attaches to either, biased by springs 769 or other biasing means. It will be appreciated that the left side of FIGS. 7B and 7C each shows an engaged configuration where the clip arm 766 is pivoted with the lower engaging portion inward/downward (which will position will be mirrored relative to the other side's matching clip in that engaged configuration), while the right side of those figures each shows a disengaged configuration where the clip arm 766 is pivoted outward/upward (which will position will be mirrored relative to the other matching clip in that disengaged configuration). In the disengaged position, the clip arms 766 pivotingly rock outward/upward such that a protruding lower lip 766*a* thereof is disengaged from below the annular lip 714*b* of the port 714. A pair of lengthwise-adjustable clamping legs 768 of the connection structure 760 fit firmly and securely to lateral sides of the base 714*c* of the accessory port 714. These legs 768 are shown extended in FIG. 7 and retracted in FIG. 7A.

As shown in FIG. 7C, when the connection structure 760 is engaged to the port 714, the miniscope handle passage 749 is aligned with and secured to the accessory channel of the larger scope 710. This will allow operation of the miniscope catheter shaft body 750 through the accessory channel. It should be appreciated that, for an accessory port like that shown in FIG. 5, the pivoting clip arms (e.g., 766) may be shaped to engage one or both of the annular lip 514*b* and annular ring 514*e*. It should also be appreciated that a locking sleeve or extension (not shown) may be provided to engage around the lower portion of the pivoting clip arms 766, assisting the biasing structure to keep them even more firmly locked in a closed/engaged position. Also, a gasket 799 or other seal-enhancing structure may be provided between the miniscope handle passage 749 and the larger scope's accessory channel 715.

Figure 8:
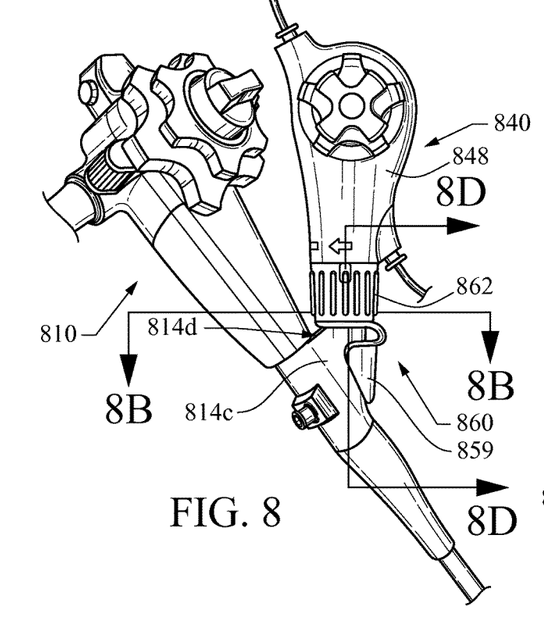
FIGS. 8-8D show a third connection structure embodiment.
Figure 8A:
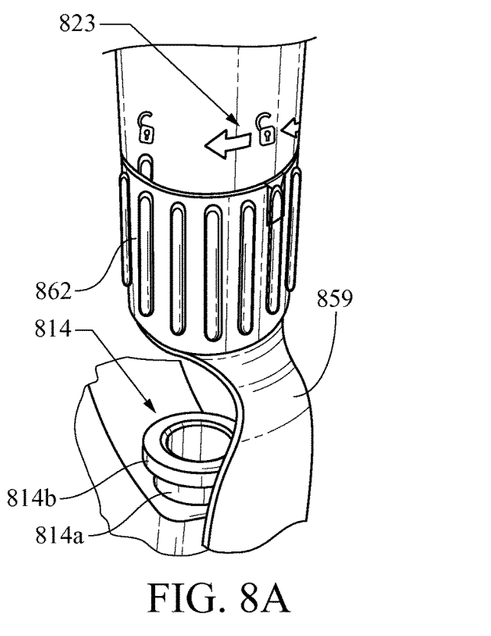

FIG. 8 shows a third connection structure embodiment 860 as part of a miniscope 840 that is securely and rigidly but removably and adjustably attached to a larger endoscope 810. FIGS. 8A-8D show the structure and function of the third embodiment of a connection structure 860, which includes a locking rotary collar 862. As shown in FIGS. 8-8A, a location/stabilization wrap 859 may be provided. As shown in FIG. 8, the wrap 859 is contoured to conform to the accessory port base 814*c* of the larger scope 810 below its flat/base surface 814*d* (identified for clarity in FIG. 8D). This feature may help a user more easily to align and connect the two scopes, as well as providing additional stability during operation.

Figure 8B:
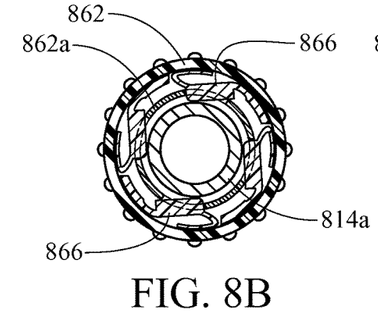
Figure 8C:
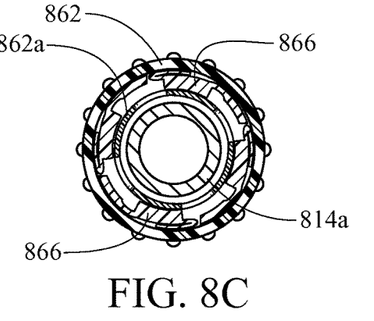
Figure 8D:
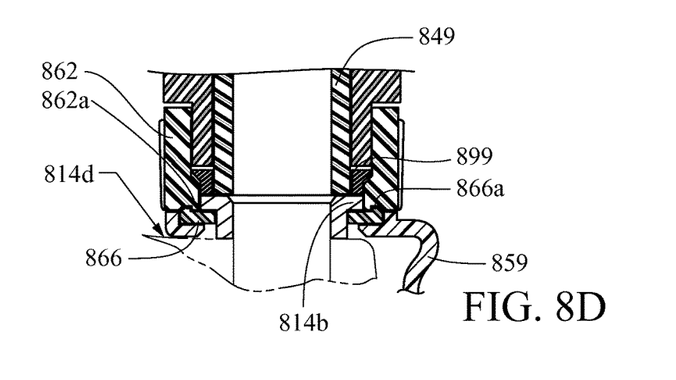

Those of skill in the art will understand and appreciate the structure and function of the connection structure 860 with reference to the external plan view of FIG. 8, the external perspective view of FIG. 8A, the transverse section views (taken along line 8B-8B of FIG. 8A) of FIGS. 8B-8C, and the longitudinal section view (taken along line 8D-8D of FIG. 8A) of FIG. 8D. A plurality of clips 866 is provided in a circle around the inner diameter of the rotary collar 862. Each of the clips 866 is biased toward the radial center of the rotary collar 862. In the illustrated embodiment, the clips 866 each include a plastic body and legs that provide, respectively, engaging and biasing structure, but those of skill in the art will appreciate—with the teaching of the present disclosure—that other clip embodiments may be constructed and practiced within the scope of the present inventive concepts, whether constructed in levered fashion as shown or in another manner.

A downward-extending central crenellated annular ring 862*a* contacts an upward protrusion 866*a* of the clips 866. Specifically, as shown in FIGS. 8B and 8C, the crennels 862*a* contact the clips 866. The view shown in FIG. 8B corresponds to the engaged configuration shown in FIG. 8D, where the clips 866 are extended to engage against the tubular body 814*a* of the larger scope's accessory port 814. As shown in FIGS. 8B and 8D, the clips 866 provide a rigid, secure engagement below the port's annular lip 814*b* (the outer contour of which is shown by a dashed line in FIGS. 8B and 8C. A gasket 899 or other seal-enhancing structure may be provided between the miniscope handle passage wall 849 and one or more components of the miniscope 840 and/or larger scope 810. The view shown in FIG. 8C corresponds to the unlocked/disengaged external view of FIG. 8A. In FIG. 8C, the rotary collar 862 has been rotated so that its crennels 862*a* contact the clips 866, compressing them and disengaging them from below the annular lip 814*b* of the larger scope's accessory port 814.

As shown in FIGS. 8 and 8A, visual or other indicia 823 may be provided to indicate the locked/engaged and/or unlocked/disengaged position of the rotary collar 862 relative to the miniscope handle body 848. It should be appreciated that tactile and/or auditory indicia may also be included (e.g., one or more detents or other shaped surfaces on and/or in the device configured to provide a "click" sound and/or feel that indicates completion of secure engagement, and that may provide a frictional lock feature as well to prevent inadvertent rotation/disengagement).

Figure 9:
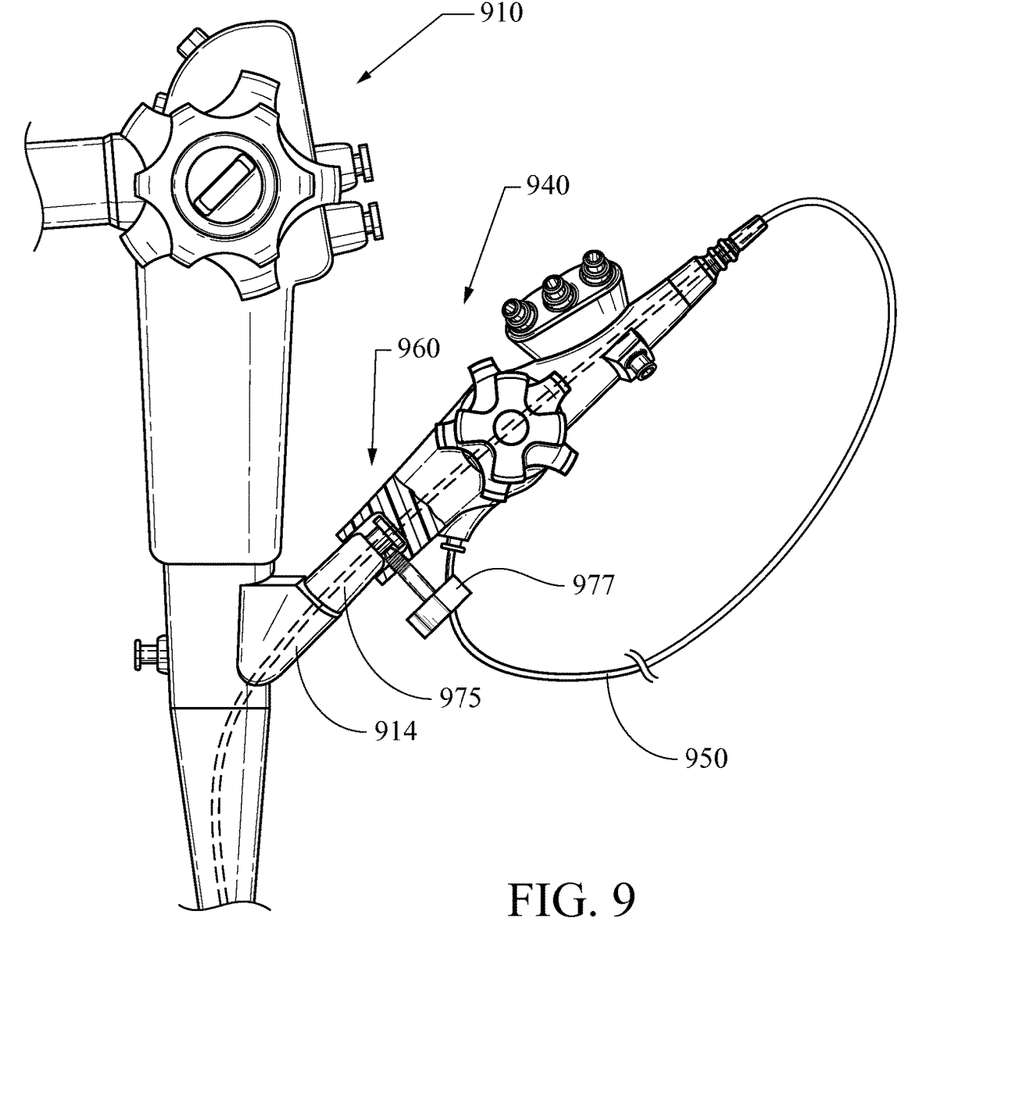
FIG. 9 shows a fourth connection structure embodiment.

In another embodiment, shown in FIG. 9, a miniscope 940 may be secured to a larger scope 910 by a connection structure 960 that includes a set-screw 977. The set screw 977 may be secured directly to the accessory port 914 of the larger scope 910 or to an intervening connector element 975 that is threadedly, frictionally, or otherwise attached to the accessory port 914. Set screws or other supplementary securement structures may be used in conjunction with other connection structures described herein to provide additional means of secure, rigid attachment to allow passage of the miniscope shaft 950 into the larger scope 910. Intervening and/or miniscope-integrated connector elements may be embodied, for example, in the manner of connector devices disclosed in U.S. Pat. No. 8,460,176 to McGrath, which is incorporated herein by reference.

Those of skill in the art will appreciate that embodiments not expressly illustrated herein may be practiced within the scope of the claims, including that features described herein for different embodiments may be combined with each other and/or with currently-known or future-developed technologies while remaining within the scope of the claims. Except where expressly set forth in said claims, embodiments presently disclosed and claimed are directed to a single endoscope and its connection mechanisms, while a second endoscope is referenced by way of environment/context for the connection mechanism's structure and function (except that certain claims specifically cite a dual-scope structure and other claims expressly claim the structure of the second endoscope as an addition to the connection mechanism of a first scope). Although specific terms are employed herein, they are used in a generic and descriptive sense only and not for purposes of limitation unless specifically defined by context, usage, or other explicit designation. It is therefore intended that the foregoing detailed description be regarded as illustrative rather than limiting. And, it should be understood that the following claims, including all equivalents, are intended to define the spirit and scope of this invention. Furthermore, the advantages described above are not necessarily the only advantages of the invention, and it is not necessarily expected that all of the described advantages will be achieved with every embodiment. In the event of any inconsistent disclosure or definition from the present application conflicting with any document incorporated by reference, the disclosure or definition herein shall be deemed to prevail.

We claim:

1. A medical endoscope, comprising:
an elongate, manipulable shaft including a distal-end visualization element; and
a handle body including a proximal handle body end longitudinally distant from a distal handle body end, and comprising at least one control surface for manipulating a distal region of the shaft, where a proximal region of the shaft extends generally distally from a portion of the handle body;
where the handle body includes a longitudinal proximal-distal passage, nearer the distal handle body end than the proximal handle body end, through which a length of the shaft is passable;
where the handle body includes a longitudinally distal connection structure that securely, rigidly, and removably mounts a distal portion of the handle body to a channel of a second endoscope in a manner axially aligning the passage with the channel to provide a path of communication for the shaft; and
where a longitudinally proximal lengthwise portion of the handle body is axially offset relative to a proximal open end of the passage and relative to the distal connection structure, such that the passage extends through less than a majority longitudinal length of the handle body.

2. The medical endoscope of claim 1, further comprising a second endoscope to which the distal connection structure provides a secure, rigid, and removable mounting connection.

3. The medical endoscope of claim 1, where the distal portion of the handle body includes the passage, which passage extends through the distal connection structure of the handle body.

4. The medical endoscope of claim 1, where the distal connection structure includes a levered clip engagement configuration.

5. The medical endoscope of claim 4, where the distal connection structure further comprises a second connection structure configured to engage another element of a second endoscope.

6. The medical endoscope of claim 1, where the distal connection structure includes connection means selected from rotary-engaged clamp, lever-engaged clamp, threaded engagement, set screw, bayonet, Luer lock, and any combination thereof.

7. The medical endoscope of claim 6, where the distal connection structure further includes connection means configured to conformingly engage into and/or around a body structure of a second endoscope.

8. The medical endoscope of claim 1, where the distal connection structure includes connection means configured to conformingly engage a body structure of a second endoscope.

9. A dual medical endoscope system, comprising:
a first medical endoscope and a second medical endoscope;
where the first medical endoscope comprises an accessory channel with a proximal mounting port providing access thereto;
where the second medical endoscope comprises a handle body that is securely, rigidly, and removably attached to the proximal mounting port by a distal handle body connection portion of the second medical endoscope;
where the handle body includes a proximal handle body portion with a first proximal-distal longitudinal axis that is offset from a second proximal-distal longitudinal axis of the distal handle body connection portion;
where the distal handle body connection portion includes a passage through which a length of the shaft is passable; and
where a proximal end of the passage opens from a surface of the distal handle body connection portion, distal of the proximal handle portion.

10. The system of claim 9, where the proximal mounting port comprises an extended tubular element with an annular lip, and the handle body receivingly engages the annular lip.

11. The system of claim 10, where the handle body is further attached by a clamp structure secured to a proximal mounting port of the first medical endoscope adjacent the annular lip.

12. The system of claim 10, where the handle body is further attached by a different clamp structure secured to a base portion of the accessory channel.

13. The system of claim 9, where the handle body is securely, rigidly, and removably attached by a clamp structure secured to a proximal end portion of the first medical endoscope.

14. The system of claim 9, further comprising an elongate, manipulable shaft including a distal-end visualization element and at least one control surface for manipulating a distal region of the shaft;
where the channel of the first endoscope is generally axially aligned with the passage of the second endoscope to provide a path of communication for the shaft into and through the channel.

15. The system of claim 14, where the shaft extends generally distally from the proximal handle body portion, through the passage of the distal handle body connection portion, and through at least a portion of the channel.

16. A method for performing a dual-endoscope procedure, the method comprising steps of:
operating a first, larger, endoscope and a second, smaller, endoscope constructed according to claim 1,
where the larger endoscope includes an accessory channel with proximal engagement structure providing direct access to the channel,
where a distal shaft of the second endoscope is sized for passage through the channel, and
where the second endoscope includes a connection structure that securely, rigidly, and removably mounts a handle of the second endoscope directly to the proximal engagement structure of the first endoscope's accessory channel; and
directing a distal shaft of the first endoscope to a target region; and
directing the distal shaft of the second endoscope through the channel of the first endoscope.

17. The method of claim 16, where the target region to which the first endoscope is directed is within a duodenum adjacent the Ampulla of Vater, and where the step of directing the distal shaft of the second endoscope through the channel further comprises directing the distal shaft of the second endoscope into the common bile duct.

18. The method of claim 16, where the method further comprises conducting one or more of endoscopic retrograde cholangiopancreatography, endoscopic retrograde cholangiography, and cholangioscopy.

19. The method of claim 16, where a user is provided with instructions to hold a body of the first endoscope in one hand and to operate manipulable controls of the first endoscope and of the second endoscope with the other hand.

20. The method of claim 16, where at least one control surface of the second endoscope is configured substantially similarly to at least one control surface of the first endoscope.

21. A medical endoscope, comprising:
an elongate, manipulable shaft including a distal-end visualization element; and
a handle body including a proximal handle body end longitudinally distant from a distal handle body end and comprising at least one proximal control surface for manipulating a distal region of the shaft;
where the handle body includes a distal connection structure through which a length of the shaft is passable along a first proximal-distal longitudinal axis that is offset from a second proximal-distal longitudinal axis of a proximal majority of the handle body; and
where the distal connection structure is configured for securely, rigidly, and removably mounting the handle to a channel of a second endoscope in a manner axially aligning a passage through the distal connection structure with the channel to provide a path of communication for the shaft.

22. The endoscope of claim 21, where the shaft extends generally distally from a portion of the handle that is proximal of or adjacent to the distal connection structure, and where the shaft is configured to loop around and extend through the passage and into the channel.

* * * * *